(12) United States Patent
Lord et al.

(10) Patent No.: US 12,220,522 B2
(45) Date of Patent: Feb. 11, 2025

(54) SYSTEM AND APPARATUS FOR AEROSOL DELIVERY AND METHODS OF MANUFACTURING

(71) Applicant: Imperial Tobacco Limited, Bristol (GB)

(72) Inventors: Christopher Lord, Liverpool (GB); Kenneth Scott, Liverpool (GB); Tom Sudlow, Liverpool (GB); David Jones, Liverpool (GB); Stephen McDonald, Liverpool (GB)

(73) Assignee: IMPERIAL TOBACCO LIMITED, Bristol (GB)

( * ) Notice: Subject to any disclaimer, the term of this patent is extended or adjusted under 35 U.S.C. 154(b) by 864 days.

(21) Appl. No.: 16/080,160

(22) PCT Filed: Feb. 15, 2017

(86) PCT No.: PCT/GB2017/050398
§ 371 (c)(1),
(2) Date: Aug. 27, 2018

(87) PCT Pub. No.: WO2017/144861
PCT Pub. Date: Aug. 31, 2017

(65) Prior Publication Data
US 2019/0046741 A1  Feb. 14, 2019

(30) Foreign Application Priority Data
Feb. 26, 2016 (GB) ...................................... 1603418

(51) Int. Cl.
*A24F 40/42* (2020.01)
*A24F 40/46* (2020.01)
(Continued)

(52) U.S. Cl.
CPC ............ *A61M 11/042* (2014.02); *A24F 40/42* (2020.01); *A24F 40/46* (2020.01); *A24F 40/70* (2020.01);
(Continued)

(58) Field of Classification Search
None
See application file for complete search history.

(56) References Cited

U.S. PATENT DOCUMENTS

| 5,746,227 A | 5/1998 | Rose |
| 2011/0041861 A1 | 2/2011 | Sebastian |

(Continued)

FOREIGN PATENT DOCUMENTS

| CA | 2925647 A1 | 4/2015 |
| CA | 2924390 A1 | 6/2015 |

(Continued)

OTHER PUBLICATIONS

International Search Report for corresponding PCT application No. PCT/GB2017/050398, dated Jul. 24, 2017.
(Continued)

*Primary Examiner* — Katherine A Will
(74) *Attorney, Agent, or Firm* — J. Miguel Hernandez; James R. Gourley; Carstens, Allen & Gourley, LLP (57) ABSTRACT

There is disclosed an aerosol delivery system comprising: an aerosol-generating device (12) comprising: —a device housing having an open-ended heating chamber configured to receive a carrier cartridge (14); —a heater element (24) disposed within the heating chamber (22) and configured to receive at least a first end of a carrier cartridge (14), said heating element operable to heat a carrier substrate of a carrier unit of said carrier cartridge (14) to cause release of an aerosol-forming precursor therefrom to generate an aerosol when gas is passed through the carrier cartridge (14);

(Continued)

and—a carrier cartridge comprising a carrier unit (34), said carrier unit comprising a carrier substrate configured to hold an aerosol-forming precursor comprising a nicotine-containing and/or flavoured fluid, gel, wax, or powder. Also disclosed are a carrier cartridge (14), carrier unit (34), methods of manufacturing one or more components of said system, and a kit-of-parts for assembling the system.

52 Claims, 8 Drawing Sheets

(51) Int. Cl.
    *A24F 40/70*     (2020.01)
    *A61M 11/00*     (2006.01)
    *A61M 11/04*     (2006.01)
    *A24F 40/10*     (2020.01)
    *A24F 40/20*     (2020.01)

(52) U.S. Cl.
    CPC .............. *A61M 11/00* (2013.01); *A24F 40/10* (2020.01); *A24F 40/20* (2020.01); *A61M 2202/064* (2013.01)

(56) References Cited

U.S. PATENT DOCUMENTS

| | | | | |
|---|---|---|---|---|
| 2014/0345633 A1* | 11/2014 | Talon | ................ | G01N 33/0004 |
| | | | | 131/329 |
| 2015/0209530 A1* | 7/2015 | White | ................ | A24D 1/20 |
| | | | | 128/200.23 |
| 2015/0351456 A1* | 12/2015 | Johnson | ................ | A24F 40/30 |
| | | | | 131/329 |
| 2016/0295916 A1* | 10/2016 | Malgat | ................ | A24D 1/20 |
| 2017/0215476 A1* | 8/2017 | Dickens | ................ | A24F 40/42 |
| 2018/0338520 A1* | 11/2018 | Sutton | ................ | A24D 1/20 |

FOREIGN PATENT DOCUMENTS

| | | |
|---|---|---|
| CN | 204217904 U | 3/2015 |
| EP | 0545186 A2 | 6/1993 |
| EP | 2404515 B1 | 9/2015 |
| EP | 3858157 A2 | 8/2021 |
| WO | 2006090290 A1 | 8/2006 |
| WO | 2009132793 A1 | 11/2009 |
| WO | 2013034488 A2 | 3/2015 |
| WO | 2015075650 A1 | 5/2015 |
| WO | 2015082652 A1 | 6/2015 |
| WO | 2015082653 A1 | 6/2015 |
| WO | 2015176898 A1 | 11/2015 |
| WO | 2015177265 A1 | 11/2015 |
| WO | 2016005600 A1 | 1/2016 |
| WO | 2016023965 A1 | 2/2016 |

OTHER PUBLICATIONS

Patent Act 1977: Search Report under Section 17(5) for corresponding application No. GB1603418.3, dated Sep. 13, 2016.
Patent Act 1977: Search Report under Section 17(6) for corresponding application No. GB1603418.3, dated Oct. 13, 2017.
Combined Search and Examination Report under Sections 17 and 18(3) for application GB2111324.6 dated Aug. 24, 2021 (5 pages).
Combined Search and Examination Report under Sections 17 and 18(3) for application GB2118524.4 dated May 11, 2022 (5 pages).

* cited by examiner

SYSTEM AND APPARATUS FOR AEROSOL DELIVERY AND METHODS OF MANUFACTURING

CROSS REFERENCE TO RELATED APPLICATION

This application is a U.S. National Phase application of, and claims the benefit of, International (PCT) Application No. PCT/GB2017/050398, filed Feb. 15, 2017. International (PCT) Application No. PCT/GB2017/050398 claims priority to GB Patent Application No. 1603418.3, filed Feb. 26, 2016.

TECHNICAL FIELD

The present invention relates to a system and apparatus for aerosol delivery and methods of manufacturing one or more components of said system. In particular, the present invention relates to a system and method for releasing an aerosol from a carrier substrate holding an aerosol-forming precursor by heating of the carrier substrate.

BACKGROUND

Aerosol delivery devices and systems fall into two broad categories: a first, non-powered category and a second, powered category.

Devices or systems in the first category may comprise nicotine replacement therapy devices such as "inhalators", e.g. Nicorette® Inhalator. Inhalators generally allow nicotine-containing aerosol to be inhaled through an elongate tube in which a container containing a nicotine carrier, for example, a substrate, is located. An air stream caused by suction through the tube by the user carries nicotine vapours into the lungs of the user to satisfy a nicotine craving. The container may comprise a replaceable cartridge, which includes a cartridge housing and a passageway in the housing in which a nicotine reservoir is located. The reservoir holds a measured amount of nicotine in the form of the nicotine carrier. The measured amount of nicotine is an amount suitable for delivering a specific number of "doses". The form of the nicotine carrier is such as to allow nicotine vapour to be released into a fluid stream passing around or through the reservoir. The passageway generally has an opening at each end for communication with the exterior of the housing and for allowing the fluid stream through the passageway. A nicotine-impermeable barrier seals the reservoir from atmosphere. The barrier includes passageway barrier portions for sealing the passageway on both sides of the reservoir. These barrier portions are frangible so as to be penetrable for opening the passageway to atmosphere.

Devices or systems in the second category can fall into two sub-categories. In both sub-categories, such devices or systems may comprise electronic devices or systems that permit a user to simulate the act of smoking by producing an aerosol mist or vapour that is drawn into the lungs through the mouth and then exhaled. The inhaled aerosol mist or vapour typically bears nicotine and/or other flavourings without, or with fewer of, the odour and health risks associated with traditional smoking and tobacco products. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

Aerosol delivery devices or systems in a first sub-category of the second, powered category generally use heat and/or ultrasonic agitation to vaporize a solution comprising nicotine and/or other flavouring, propylene glycol and/or glycerine-based base into an aerosol mist of vapour for inhalation.

Aerosol delivery devices or systems in a second sub-category of the second, powered category may typically comprise devices or systems in which tobacco is heated rather than combusted. During use, volatile compounds may be released from the tobacco by heat transfer from the heat source and entrained in air drawn through the aerosol delivery device or system. Direct contact between a heat source of the aerosol delivery device or system and the tobacco heats the tobacco to form an aerosol. As the aerosol containing the released compounds passes through the device, it cools and condenses to form an aerosol for inhalation by the user. In such devices or systems, heating, as opposed to burning, the tobacco may reduce the odour and health risks that can arise through combustion and pyrolytic degradation of tobacco.

Although use of aerosol delivery devices or systems of the second sub-category of powered devices or systems may have fewer associated health risks than use of traditional smoking or tobacco products, the health risks to users may be greater than those experienced through use of aerosol delivery devices or systems of the first sub-category of powered devices or systems. However, aerosol delivery devices or systems of the second sub-category of powered devices or systems may be preferable over those of the first sub-category to some users because of the user experience that devices in this sub-category provide, i.e. a perceived similar satisfaction and perceived similar physical sensations to those experienced from using a traditional smoking or tobacco product. These similarities may be perceived due to the user inhaling a warmed aerosol resulting from the heating of tobacco.

Aerosol delivery devices or systems falling into the second sub-category of powered devices or system may typically comprise a powered unit, comprising a heating element, into which can be inserted a cartridge comprising tobacco. The cartridge may resemble a traditional cigarette and may be generally cylindrical in form with a "mouthpiece" at one end through which the user can draw the aerosol mist or vapour for inhalation. The heating element penetrates an end of the cartridge remote from the mouthpiece end and directly contacts the tobacco within the cartridge. The cartridge may provide for a limited number of inhalations or "puffs" before the tobacco content is depleted. The cartridges, therefore, are disposable and replaceable.

A potential drawback associated with aerosol delivery devices or systems falling within the second sub-category of powered devices or systems may arise due to heating of tobacco. Whilst the health risks to users of such devices may be lessened somewhat compared to use of traditional smoking or tobacco products, potentially harmful by-products may be released during the heating of tobacco and so some health risks may remain.

A further potential drawback may arise due to the arrangement of the tobacco around the heating element when the cartridge is in-situ in the device. It may not be possible to achieve uniform heating of the tobacco across the width of the cartridge, because of a decreasing temperature gradient away from the heating element. That is, tobacco in direct contact with the heating element will be heated by a greater amount than tobacco that is further away from the heating element. To ensure that volatile compounds are extracted from all of the tobacco in the cartridge, the heating element must be heated by an amount to ensure that heat sufficient to cause release of the volatile compounds from the tobacco reaches even the outermost parts of the tobacco "charge". However, the temperature that the heating element provides to ensure that the outermost regions of the tobacco "charge" are heated sufficiently may be great enough to cause pyrolysis in regions of the tobacco "charge" that directly contact or are closer to the heating element.

Aspects and embodiments of the invention were devised with the foregoing in mind.

BRIEF SUMMARY OF THE PRESENT INVENTION

According to an aspect of the present invention, there is provided an aerosol delivery system comprising:
an aerosol-generating device comprising:
a device housing having an open-ended heating chamber configured to receive a carrier cartridge;
a heater element disposed within the heating chamber and configured to receive at least a first end of a carrier cartridge, said heating element operable to heat a carrier substrate of a carrier unit of said carrier cartridge to cause release of an aerosol-forming precursor therefrom to generate an aerosol when gas is passed through the carrier cartridge; and
a carrier cartridge comprising a carrier unit, said carrier unit comprising a carrier substrate configured to hold an aerosol-forming precursor comprising a nicotine-containing and/or flavoured fluid, gel, wax, or powder.

Optionally, the heating element may be configured to penetrate the carrier substrate.

Optionally, the carrier substrate may comprise a sheet material formed from heat-resistant material.

Employing a heat-resistant material may prevent degradation (e.g. by pyrolysis) occurring in the substrate material when heat is applied to the substrate material. This is because production of smoke (caused by pyrolysis of a substrate matrix material) may be undesirable.

Optionally, the sheet material may be folded in a substantially concertina arrangement.

Optionally, the sheet material may be folded in a random manner to form folds of said sheet material that are randomly oriented with respect to other files of said sheet material.

Optionally, the substrate may comprise a plurality of layers of sheet material, each layer oriented in a random manner with respect to other layers of said material.

Optionally, the carrier cartridge may be tubular and may comprise sheet material, and wherein a second end of the carrier cartridge may be configured to form a mouthpiece for a user.

Optionally, the heat-resistant material may comprise a paper or paper matrix composite.

Optionally, the heat-resistant material may comprise a plastic or plastic matrix composite.

Optionally, the heat-resistant material may comprise comprises a ceramic or ceramic matrix composite.

The ceramic or ceramic matrix composite may provide a level of resilience to prevent damage to the substrate during insertion of the heater element into the aerosol carrier cartridge. This resilience may also assist with easing insertion of the heater element into the substrate of the aerosol carrier cartridge, because the material may deflect away from the heater element as it is being inserted, but return back towards its starting point to form a contact around the heater element, when so inserted. This may enhance the thermal contact of the substrate to the heater element and may improve heat transfer from the heater element to the substrate of the aerosol carrier cartridge.

Further optionally, the ceramic composite may comprise alumina-silicate fibres.

Optionally, the carrier substrate may be impregnated with said aerosol-forming precursor.

Optionally, the carrier substrate may be coated with said aerosol-forming precursor.

Optionally, the carrier substrate may be configured to hold and release extracts from a tobacco plant.

Optionally, the carrier cartridge may comprise a cooling element disposed adjacent to the carrier unit for cooling fluid released from said aerosol-forming precursor during heating.

Optionally, the cooling element may comprise a plurality of cooling formations.

Optionally, the carrier cartridge may further comprise a housing for said carrier unit, or said carrier unit and said cooling element.

Optionally, an exterior surface of the carrier unit may be formed from heat-resistant material configured to surround said carrier substrate.

Optionally, the carrier unit may comprise a first substrate comprising the aerosol-generating precursor and a thermally conductive second substrate configured to conduct heat from the heater element to the first substrate to cause release of said aerosol-forming precursor therefrom.

Optionally, the first substrate may comprise an annular ring disposed around the second substrate.

Optionally, the second substrate may comprise an opening for receiving the heating element.

Optionally, the carrier unit may further comprise an isolation layer that separates the first substrate and the second substrate to isolate the heating element from aerosol-generating precursor.

According to another aspect of the present invention, there is provided a carrier cartridge for a system for aerosol delivery, the carrier cartridge at an end thereof configured for insertion into a heating chamber of a device operative to initiate and maintain release of an aerosol from a carrier unit in said carrier cartridge, and another end of said carrier cartridge configured for insertion into a mouth of a user, the carrier cartridge comprising:
a carrier unit, said carrier unit comprising a carrier substrate configured to hold an aerosol-forming precursor comprising a nicotine-containing and/or flavoured fluid, gel, wax, or powder.

Optionally, the carrier substrate may be configured to be penetrable by a heater element of said device.

Optionally, the carrier substrate may comprise sheet material formed from heat-resistant material.

Optionally, the sheet material may be folded in a substantially concertina arrangement.

Optionally, the sheet material may be folded in a random manner to form folds of said sheet material that are randomly oriented with respect to other files of said sheet material.

Optionally, the substrate may comprise a plurality of layers of sheet material, each layer oriented in a random manner with respect to other layers of said material.

Optionally, the carrier cartridge may be tubular and may comprise sheet material, and wherein a second end of the carrier cartridge is configured to form a mouthpiece for a user.

Optionally, the heat-resistant material may comprise a paper or paper matrix composite.

Optionally, the heat-resistant material may comprise a plastic or plastic matrix composite.

Optionally, the heat-resistant material may comprise a ceramic or ceramic matrix composite.

Optionally, the ceramic composite may comprise alumina-silicate fibres.

Optionally, the carrier substrate may be impregnated with said aerosol-forming precursor.

Optionally, the carrier substrate may be coated with said aerosol-forming precursor.

Optionally, the carrier substrate may be configured to hold and release extracts from a tobacco plant.

Optionally, the carrier cartridge may comprise a cooling element disposed adjacent to the carrier unit for cooling fluid released from said aerosol-forming precursor during heating.

Optionally, the cooling element may comprise a plurality of cooling formations.

Optionally, the carrier cartridge may further comprise a housing for said carrier unit, or for said carrier unit and said cooling element.

Optionally, an exterior surface of said carrier unit may be formed from heat-resistant material configured to surround said carrier substrate.

Optionally, the carrier unit may comprise a first substrate comprising said aerosol-generating precursor and a thermally conductive second substrate configured to conduct heat from the heater element to the first substrate to cause release of said aerosol-forming precursor therefrom.

Optionally, the first substrate may comprise an annular ring disposed around the second substrate.

Optionally, the second substrate may comprise an opening for receiving the heating element.

Optionally, the carrier unit may further comprise an isolation layer that separates the first substrate and the second substrate to isolate the heating element from aerosol-generating precursor.

According to another aspect of the present invention, there is provided a carrier unit for a nicotine carrier cartridge, the nicotine carrier unit comprising a carrier substrate that comprises an aerosol-forming precursor comprising a nicotine-containing and/or flavoured fluid, gel, wax, or powder.

Optionally, the carrier substrate may be configured to be penetrable by a heater element of a device operative to initiate and maintain release of an aerosol from said carrier unit.

Optionally, the carrier substrate may comprise sheet material formed from heat-resistant material.

Optionally, the sheet material may be folded in a substantially concertina arrangement.

Optionally, the sheet material may be folded in a random manner to form folds of said sheet material that are randomly oriented with respect to other files of said sheet material.

Optionally, the substrate may comprise a plurality of layers of sheet material, each layer oriented in a random manner with respect to other layers of said material.

Optionally, the heat-resistant material may comprise a paper or paper matrix composite.

Optionally, the heat-resistant material may comprise a plastic or plastic matrix composite.

Optionally, the heat-resistant material may comprise a ceramic or ceramic matrix composite.

Optionally, the ceramic composite may comprise alumina-silicate fibres.

Optionally, the carrier substrate may be impregnated with said aerosol-forming precursor.

Optionally, the carrier substrate may be coated with said aerosol-forming precursor.

Optionally, the carrier substrate may be configured to hold and release extracts from a tobacco plant.

Optionally, an exterior surface of said carrier unit may be formed from heat-resistant material configured to surround said carrier substrate.

Optionally, the carrier unit may comprise a first substrate comprising said aerosol-generating precursor and a thermally conductive second substrate configured to conduct heat from a heater element of a device operative to initiate and maintain release of an aerosol from said carrier unit to the first substrate to cause release of said aerosol-forming precursor therefrom.

Optionally, the first substrate may comprise an annular ring disposed around the second substrate.

Optionally, the second substrate may comprise an opening for receiving the heater element.

Optionally, the carrier unit may further comprise an isolation layer that separates the first substrate and the second substrate to isolate the heater element from aerosol-generating precursor.

According to another aspect of the present invention, there is provided a method of manufacturing a sheet material for forming a carrier substrate of a carrier unit, comprising:
    combining, to form a mixture, a sheet precursor material and an aerosol-forming precursor comprising a nicotine-containing and/or flavoured fluid, gel, wax, or powder;
    forming from said mixture a sheet material.

Optionally, said sheet material may comprise a heat-resistant sheet material.

According to another aspect of the present invention, there is provided a method of manufacturing a carrier unit, comprising folding sheet material manufactured as described above and hereinafter in at least one of: a substantially concertina arrangement; and a random manner to form folds of said sheet material that are randomly oriented with respect to other files of said sheet material.

Optionally, the method may further comprise layering a plurality of layers of said sheet material, each layer oriented in a random manner with respect to other layers of said material.

Optionally, said sheet material may comprise at least one of: a paper or paper matrix composite.

Optionally, said sheet material may comprise at least one of: a paper or paper matrix composite; a plastic or plastic matrix composite; and a ceramic or ceramic matrix composite.

Optionally, the ceramic composite or ceramic matrix composite may comprise alumina-silicate fibres.

Optionally, the method may further comprise impregnating said sheet material with an aerosol-forming precursor.

Optionally, the method may further comprise coating said sheet material with an aerosol-forming precursor.

Optionally, the aerosol-forming precursor may comprise extracts from a tobacco plant.

Optionally, the method may further comprise forming an exterior surface of said carrier unit from heat-resistant material configured to surround said sheet material.

Optionally, the method may further comprise forming a first substrate comprising an aerosol-generating precursor and forming a thermally conductive second substrate configured to conduct heat to the first substrate to cause release of said aerosol-forming precursor therefrom.

Optionally, the first substrate may comprise an annular ring disposed around the second substrate.

Optionally, the method may further comprise forming an opening in said second substrate for receiving a heater element of a device operative to initiate and maintain release of an aerosol from said carrier unit.

Optionally, the method may further comprise forming an isolation layer between said first substrate and said second substrate.

According to another aspect of the present invention, there is provided a kit-of-parts for assembling a system for aerosol delivery, comprising:

an aerosol-generating device comprising:
- a device housing having an open-ended heating chamber configured to receive a carrier cartridge;
- a heater element disposed within the heating chamber and configured to receive at least a first end of a carrier cartridge, said heating element operable to heat a carrier substrate of a carrier unit of said carrier cartridge to cause release of an aerosol-forming precursor therefrom to generate an aerosol when gas is passed through the carrier cartridge; and a carrier cartridge comprising a carrier unit, said carrier unit comprising a carrier substrate configured to hold an aerosol-forming precursor comprising a nicotine-containing and/or flavoured fluid, gel, wax, or powder.

BRIEF DESCRIPTION OF THE DRAWINGS

One or more embodiments in accordance with aspects of the present invention will be described, by way of example only, and with reference to the following drawings in which.

DETAILED DESCRIPTION OF THE INVENTION

In general outline, one or more embodiments in accordance with the present invention provide a system for aerosol delivery in which an end, or an end portion, of an aerosol carrier cartridge may be inserted into a heating chamber of a device for initiating and maintaining release of an aerosol from the aerosol carrier cartridge. Another end, or another end portion, of the aerosol carrier cartridge protrudes from the device and can be inserted into the mouth of a user for the inhalation of aerosol released from the aerosol carrier cartridge during operation of the device.

Hereinafter, and for convenience only, "system for aerosol delivery" shall be referred to as "aerosol delivery system".

Figure 1:
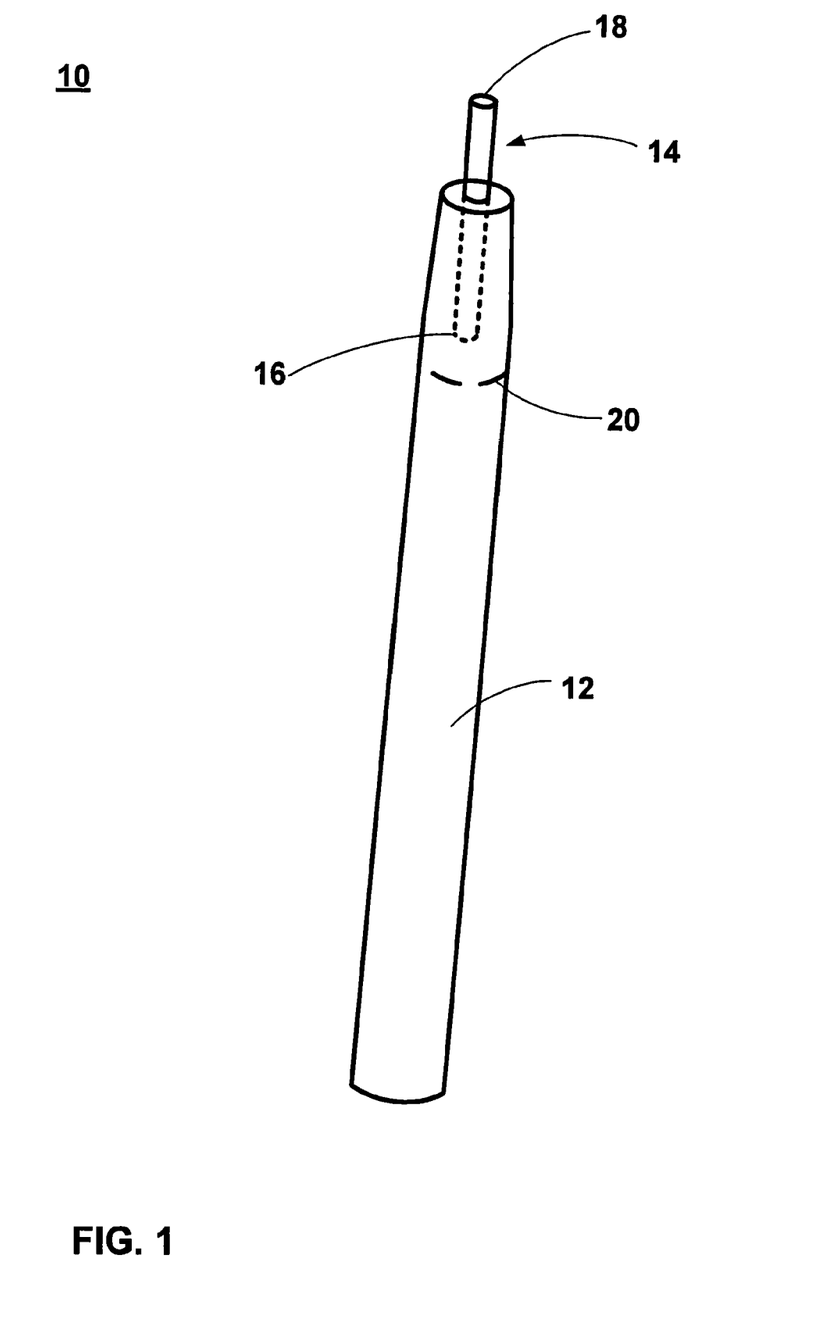
FIG. 1 is a perspective view illustration of a system for aerosol delivery according to one or more embodiments of the present invention.

Referring now to FIG. 1, there is a perspective view of an aerosol delivery system 10 comprising a device 12 operative to initiate and maintain release of aerosol from a carrier unit in an aerosol carrier cartridge and an aerosol carrier cartridge 14. In FIG. 1, the aerosol carrier cartridge 14 is shown with a first end 16 thereof and a portion of the length of the aerosol carrier cartridge 14 located within a heating chamber of the device 12. A remaining portion of the aerosol carrier cartridge 14 extends out of the heating chamber. This remaining portion of the aerosol carrier cartridge 14, terminating at a second end 18 of the aerosol carrier cartridge, is configured for insertion into a user's mouth. A vapour and/or aerosol is produced when a heater element (not shown) of the device 12 heats an aerosol carrier unit in the aerosol carrier cartridge 14 to release a vapour and/or an aerosol, and this can be delivered to the user, when the user sucks or inhales, via a fluid passage through the aerosol carrier cartridge 14 from the aerosol carrier unit to the second end 18.

The device 12 also comprises air-intake apertures 20 in the housing of the device 12 to provide a passage for air to be drawn into the interior of the device 12 (when the user sucks or inhales) for delivery to the first end 16 of the aerosol carrier cartridge 14, so that the air can be drawn through the aerosol carrier cartridge 14 during use. Optionally, these apertures may be perforations in the housing of the device 12.

An aerosol carrier unit (not shown in FIG. 1, but see FIGS. 5 and 6), such as, for example, an aerosol capsule, is located at the first end 16 of the aerosol carrier cartridge 14. The carrier unit contains at least one of: nicotine; a nicotine precursor material; a nicotine compound; and one or more flavourings, and is configured to allow air drawn into the aerosol carrier cartridge 14 from the first end 16 to flow therethrough. The nicotine, nicotine precursor material, nicotine compound, and/or one or more flavourings may be contained in an aerosol precursor material. The aerosol precursor material may comprise one or more of: a fluid; a gel; a wax; or a powder. As air passes through the carrier unit, an aerosol may be entrained in the air stream from a carrier substrate within the aerosol carrier unit bearing the nicotine, nicotine precursor material, nicotine compound and/or one or more flavourings, e.g. via diffusion.

The aerosol carrier cartridge 14 is removable from the device 12 so that it may be disposed of when expired. After removal of a used aerosol carrier cartridge 14 a replacement aerosol carrier cartridge 14 can be inserted into the device 12 to replace the used aerosol carrier cartridge 14.

Figure 2:
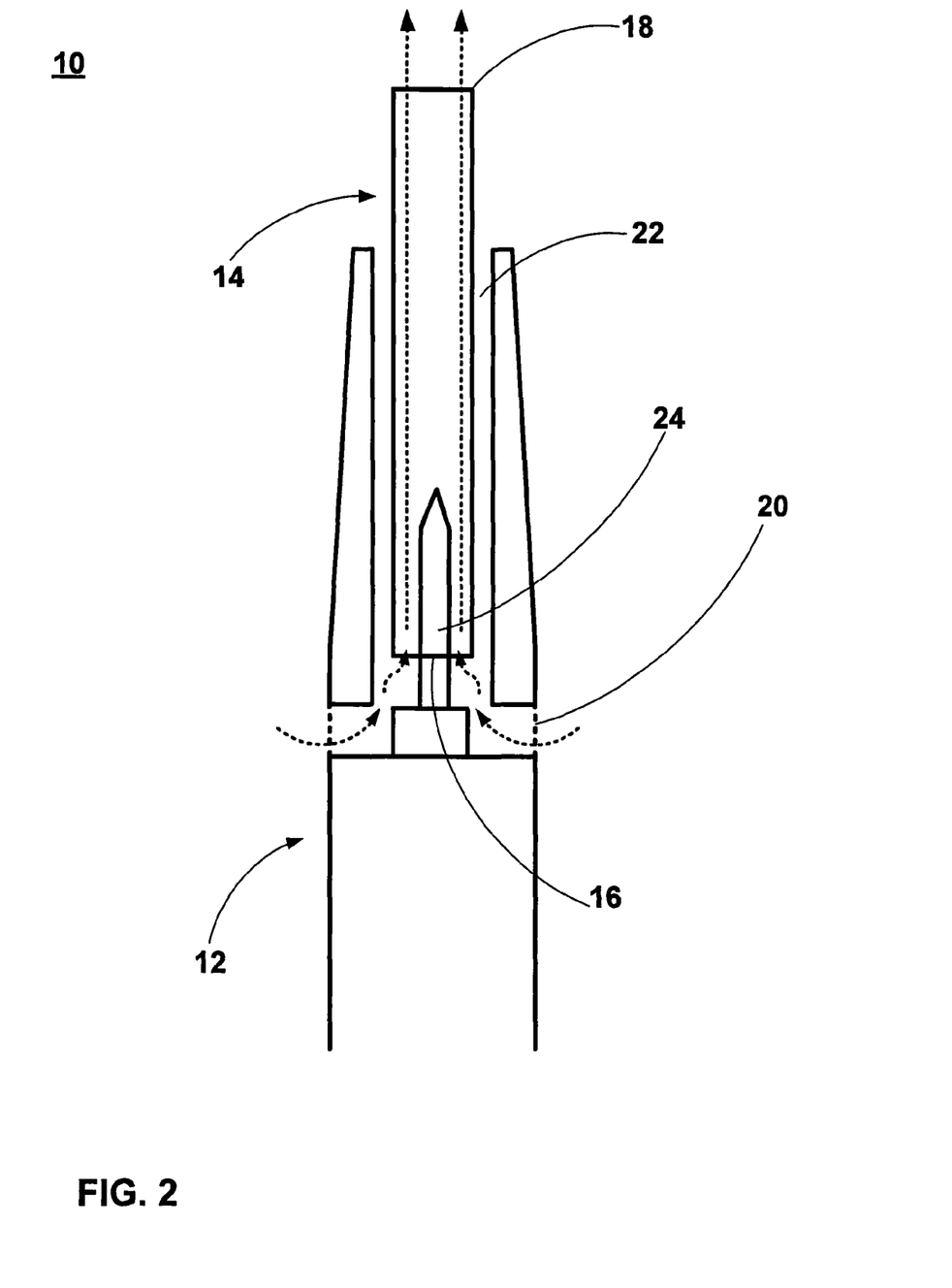
FIG. 2 is a cross-sectional side view illustration of part of a device of the system for aerosol delivery of FIG. 1.

FIG. 2 is a cross-sectional side view illustration of a part of device 12 of the aerosol delivery system 10.

The device 12 comprises a heating chamber 22 in which is located a portion of the aerosol carrier cartridge 14. The device 12 also comprise a heater element 24, which extends into the heating chamber 22, and which is configured to penetrate the aerosol carrier cartridge 14 through the first end 16 of the aerosol carrier cartridge 14.

The aerosol carrier cartridge 14 can be inserted into the heating chamber 22 such that the heater element 24 penetrates the first end 16 of the aerosol carrier cartridge 14 and extends into the aerosol carrier unit (not shown) of the aerosol carrier cartridge 14.

As described above, air flows into the device 12 (in particular, into a closed end of the heating chamber 22) via the air-intake apertures 20. From the closed end of the heating chamber 22, the air is drawn through the aerosol carrier cartridge 14 (under the action of the user inhaling or sucking on the second end 18) and expelled at second end 18. As the air flows through the aerosol carrier unit (heated by operation of the heater element 14), aerosol released, or liberated, from the aerosol carrier unit through the heating action, is drawn from the material of the aerosol carrier unit by the air flowing therethrough and is transported in the air flow to the second end 18. The direction of air flow is illustrated by arrows in FIG. 2.

To achieve release of the captive aerosol from the aerosol carrier unit, the aerosol carrier unit of the aerosol carrier cartridge 14 is heated by the heater element 24. As a user sucks or inhales on second end 18 of the aerosol carrier cartridge 14, the aerosol released from the aerosol carrier unit is drawn through the aerosol carrier cartridge 14 towards the second end 18 and onwards into the user's mouth.

Figure 3:
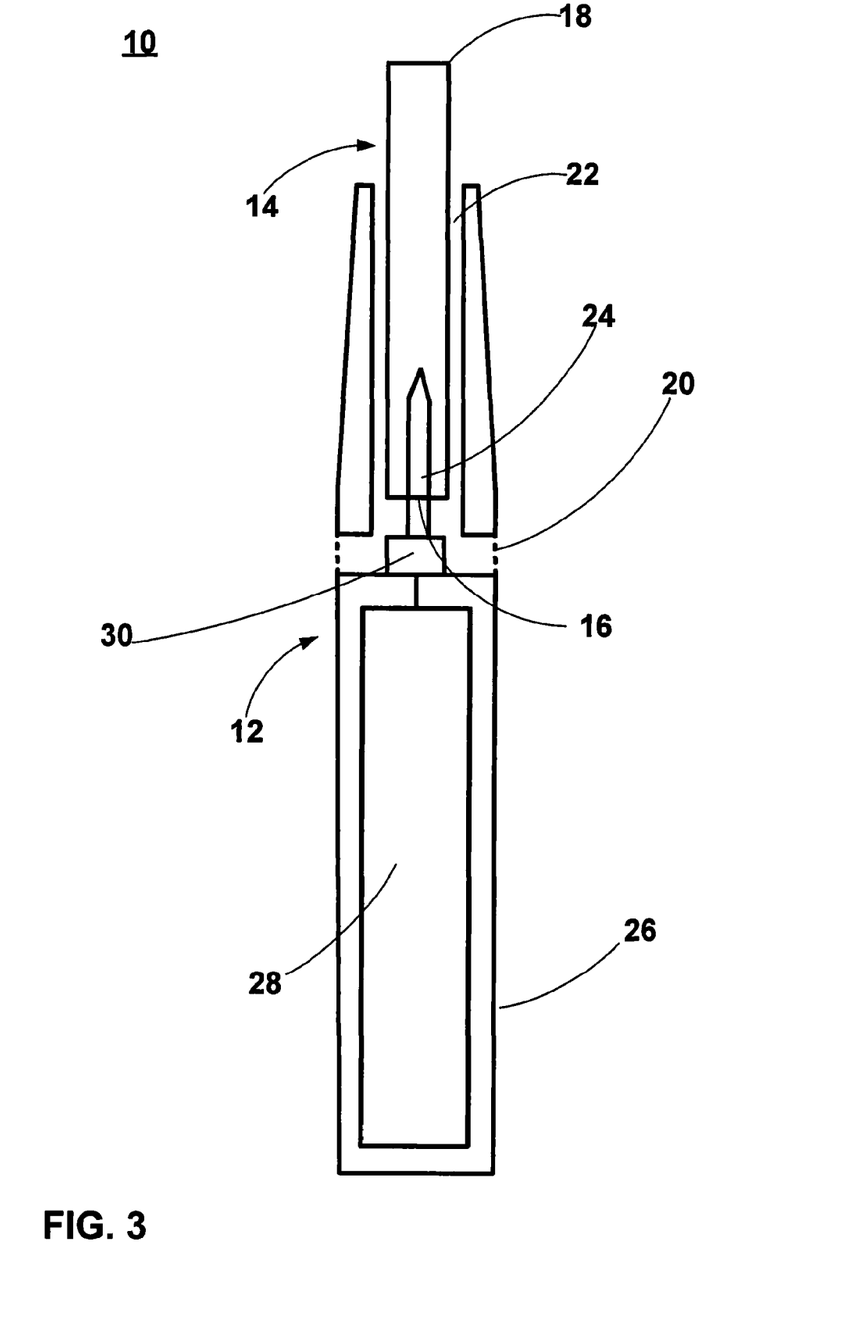
FIG. 3 is a cross-sectional side view illustration of the system and device for aerosol delivery of FIG. 1.

Turning now to FIG. 3, a cross-sectional side view of the aerosol delivery system 10 is schematically illustrated showing the features described above in relation to FIGS. 1 and 2 in more detail.

As can be seen, device 12 comprises a housing 26, in which are located the heating chamber 22 and heater element 24. The housing 26 also contains control circuitry (not shown) operative by a user, or upon detection of air and/or vapour being drawn into the device 12 through air-intake apertures 20, i.e. when the user sucks or inhales. Additionally, the housing 26 comprises an electrical energy supply 28, for example a battery. Optionally, the battery comprises a rechargeable lithium ion battery. The housing 26 also comprises a coupling 30 for electrically (and optionally mechanically) coupling the electrical energy supply 28 to control circuitry (not shown) for powering and controlling operation of the heater element 24.

Responsive to activation of the control circuitry of device 12, the heater element 24 heats the aerosol carrier unit (not shown) of aerosol carrier cartridge 14. This heating process initiates (and, through continued operation, maintains) release of vapour and/or an aerosol from the aerosol carrier unit. The vapour and/or aerosol formed as a result of the heating process is entrained into a stream of air being drawn therethrough (as the user sucks or inhales). The stream of air with the entrained vapour and/or aerosol exits the aerosol carrier cartridge 14 at second end 18 for delivery to the user.

This process is briefly described above in relation to FIG. 2, where arrows schematically denote the flow of the air stream into the device 12 and through the aerosol carrier cartridge 14, and the flow of the air stream with the entrained vapour and/or aerosol through the aerosol carrier cartridge 14.

Figure 4:
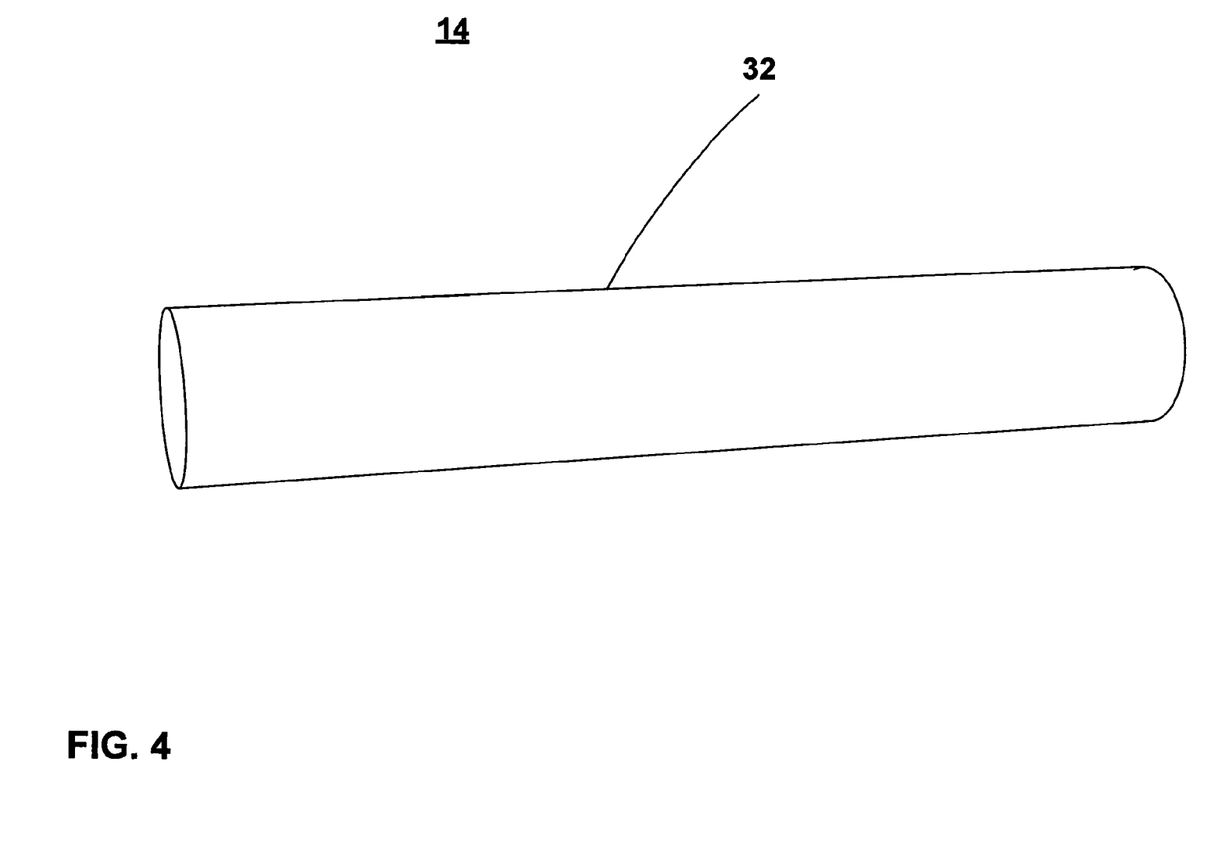
FIG. 4 is a perspective view illustration of an aerosol carrier cartridge for use in the system for aerosol delivery according to one or more embodiments of the present invention.
Figure 5:
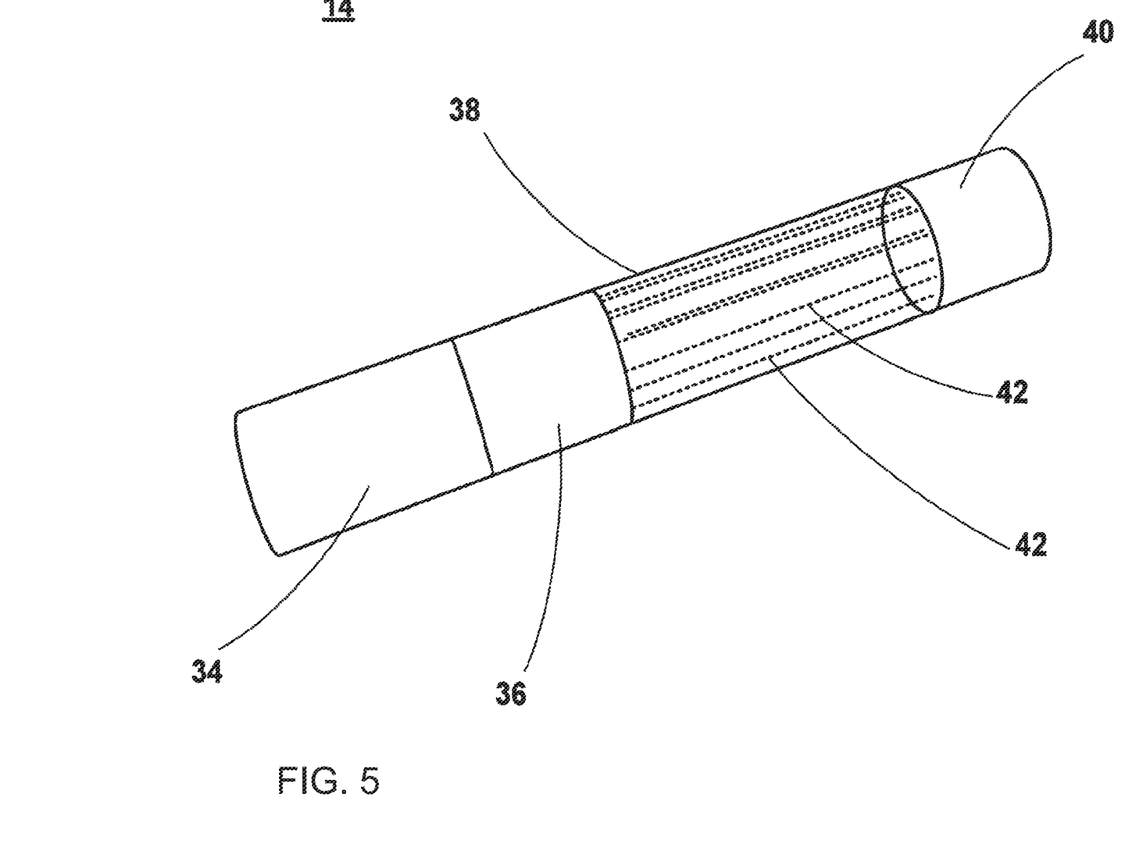
FIG. 5 is perspective view illustration of internal elements of the aerosol carrier cartridge of FIG. 4.
Figure 6:
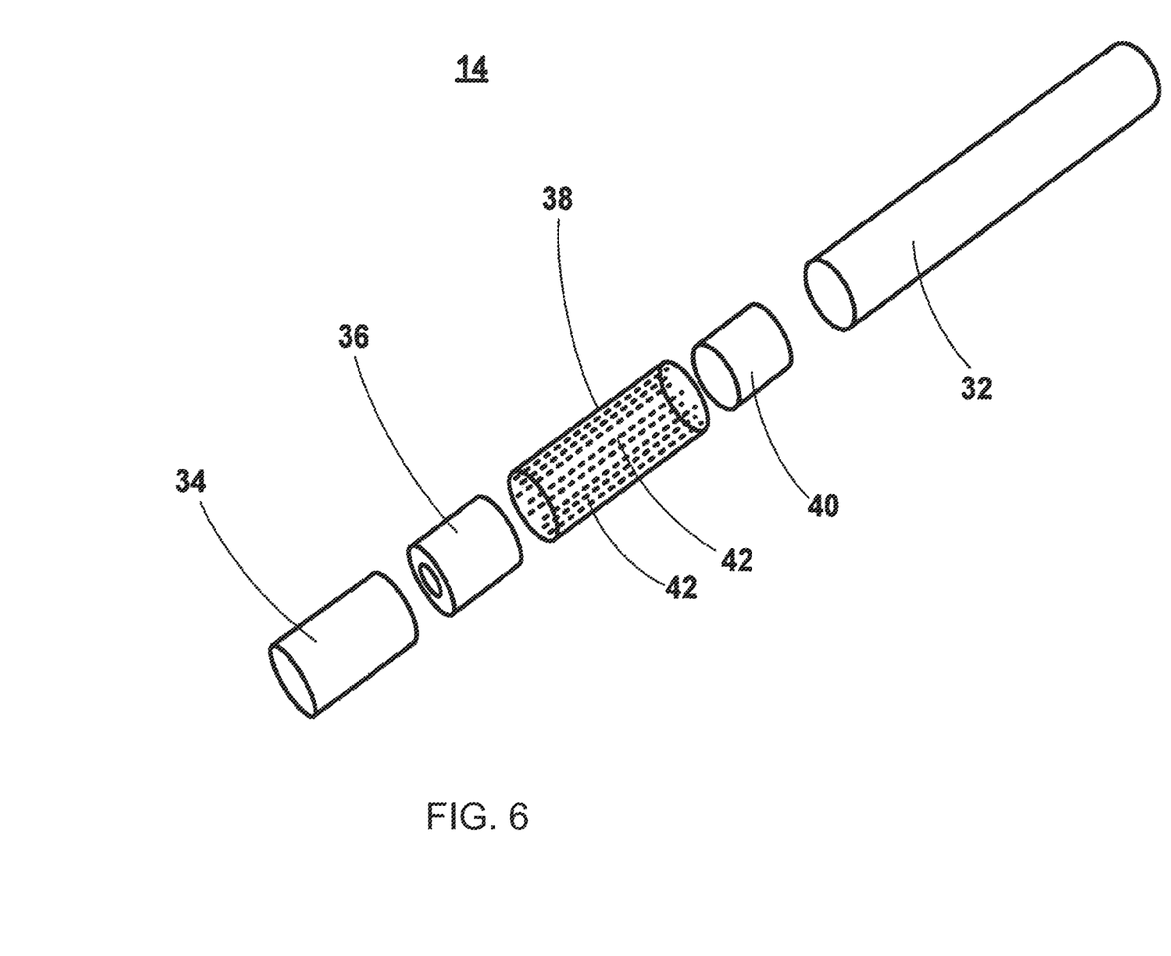
FIG. 6 is an exploded perspective view illustration of the aerosol carrier cartridge of FIG. 4.

FIGS. 4 to 6 schematically illustrate the aerosol carrier cartridge 14 in more detail. FIG. 4 illustrates an exterior of the aerosol carrier cartridge 14, FIG. 5 illustrates internal components of the aerosol carrier cartridge 14 in one or more embodiments of the present invention, and FIG. 6 illustrates all components of the aerosol carrier cartridge 14 in an exploded view.

FIG. 4 illustrates the exterior of the aerosol carrier unit 14, which comprises housing 32 for housing said aerosol carrier unit (not shown) and at least one other internal component. The housing 32 comprises a hollow tubular member, or sleeve, which may be cylindrical in form.

FIG. 5 illustrates internal components of the aerosol carrier cartridge 14. As described above, the aerosol carrier cartridge 14 comprises an aerosol carrier unit 34, but optionally may also further comprise a cooling element. Further optional components may comprise a compression-resistant spacer and/or a filter element. In an optional arrangement, the aerosol carrier cartridge 14 comprises the aerosol carrier unit 34 only. In another optional arrangement, the aerosol carrier cartridge 14 comprises the aerosol carrier unit 34 and the cooling element. In yet another optional arrangement, the aerosol carrier cartridge 14 comprises the aerosol carrier unit 34, the cooling element and at least one of the compression-resistant spacer and the filter element.

In FIG. 5, aerosol carrier cartridge 14 is shown as comprising the aerosol carrier unit 34, a compression-resistant spacer 36, a cooling element 38 and a filter element 40 in coaxial alignment. As can be seen, the components are arranged sequentially such that a first end of the compression-resistant spacer 36 abuts a second end of the aerosol carrier unit 34, a first end of the cooling element 38 abuts a second end of the compression-resistant spacer 36 and a first end of the filter element 40 abuts a second end of the cooling element 38. A first end of the aerosol carrier unit 34 corresponds to the first end of the aerosol carrier cartridge 14 and a second end of the filter element 40 corresponds to the second end of the aerosol carrier cartridge.

Housing 32 of the aerosol carrier cartridge 14 (illustrated in FIG. 4) is configured to house the components illustrated in FIG. 5.

The aerosol carrier unit 34 is located at an "upstream" end of the aerosol carrier cartridge 14.

For the avoidance of doubt, the term "upstream" defines a position towards the point at which air will be drawn into the aerosol carrier cartridge 14 when it is in use, i.e. a point from which air is drawn into aerosol carrier cartridge 14 from an interior of the device 12 (but which has been drawn into the device 12 from atmosphere). The term "downstream" defines a position from the point at, or after, which air containing the vapour and/or aerosol exits the aerosol carrier cartridge 14.

In one or more embodiments of the present invention, the aerosol carrier unit 32 comprises a substrate that holds aerosol-forming precursor. The precursor may comprise nicotine and/or flavours. The precursor may comprise at least one of: fluid; gel; wax; and powder. The substrate optionally may comprise a heat-resistant carrier material. Employing a heat-resistant carrier may prevent pyrolysis occurring in the substrate material. This is because production of smoke (caused by pyrolysis of a substrate matrix material) may be undesirable. The heat-resistant carrier optionally may comprise a plurality of pores and/or spaces and/or channels and/or conduits for holding the aerosol-forming precursor. In one or more embodiments, the aerosol-forming precursor comprises nicotine and/or nicotine compounds and/or flavours. The precursor material is configured to release an aerosol and/or vapour upon heating. Thus, as the substrate matrix material containing the precursor material is heated, the substances within the precursor material, and captively held, are released into an air stream flowing through the nicotine carrier unit 34 as an aerosol and/or vapour.

Optionally, the precursor material comprises a tobacco-plant extract material. The tobacco-plant extract material may comprise nicotine-containing wax extracted from a tobacco-plant starting material. The nicotine-containing wax may also include flavours. The tobacco-plant extract material may be extracted from tobacco plant starter material using a supercritical fluid extraction process, which may employ a conventional supercritical fluid extraction process or otherwise.

The substrate optionally comprises a sheet material formed from the heat-resistant carrier material. This sheet material may be folded in a random manner to form folds of said sheet material that are randomly oriented with respect to other folds of said sheet material (e.g. with spaces between adjacent layers caused by the folding providing the spaces, conduits and/or channels). Alternatively, or additionally, the sheet material may comprise a plurality of layers of sheet material formed from the heat-resistant carrier material, each layer oriented in a random manner with respect to other layers of said material. Again, spaces between adjacent layers may provide the spaces, conduits and/or channels.

The configuration of the sheet material of the heat-resistant carrier to include at least one of pores, spaces, channels and conduits, may provide multiple entry points (and insertion paths) to lessen the force required to insert the heater element 24 of the device 12 into the aerosol carrier cartridge 14. That is, they may ease an insertion of the heater element 24 into the aerosol carrier cartridge 14. Additionally, providing multiple layers (through folding a single sheet, layering multiple sheets, or a combination of the two) and orienting the layers in a random manner to provide the pores, spaces, conduits and/or channels, permit air to flow through the substrate of the aerosol carrier unit 34 and also increase the surface area of the substrate that is available for contact with a flow of air therethrough.

The heat-resistant carrier may comprise a ceramic material, optionally a ceramic matrix composite, further optionally ceramic paper, and yet further optionally alumina-silicate fibres. The ceramic material may provide a level of resilience to prevent damage to the substrate during insertion of the heater element 24 into the aerosol carrier cartridge 14. This resilience may also assist with easing insertion of the heater element 24 into the substrate of the aerosol carrier cartridge 14, because the material may deflect away from the heater element 24 as it is being inserted, but return back towards its starting point to form a contact around the heater element 24, when so inserted. This may enhance the thermal contact of the substrate to the heater element 24 and may improve heat transfer from the heater element 24 to the substrate of the aerosol carrier cartridge 14.

The aerosol carrier unit 34 may further comprise a sheet of heat-resistant material surrounding the substrate. Optionally, this heat-resistant material may comprise the same material as the heat resistant carrier of the substrate, but other heat-resistant materials may also be suitable.

The substrate material for the aerosol carrier unit 34 may be manufactured by combining a heat-resistant carrier precursor material and a tobacco-plant extract material such as the wax referred to earlier to form a mixture. From the mixture, a sheet material may be formed that comprises the heat-resistant carrier that holds the tobacco-plant extract material. As described above, the tobacco-plant extract material may be extracted from tobacco plant starter material using a supercritical fluid extraction process. Optionally, the substrate material for the aerosol carrier unit 34 may be manufactured by adding constituent materials for forming the heat-resistant material to constituent materials for forming the aerosol-forming precursor (i.e. comprising constituent materials for forming the heat-resistant material may be added to a nicotine-containing and/or flavoured fluid, gel, wax, or powder). Both sets of materials are mixed to form a mixture and then the mixture is formed into a sheet to form said sheet material. The constituent materials for forming the heating-resistant material may comprise alumina fibres and/or silica fibres and/or alumina powder and/or silica powder.

Manufacture of the aerosol carrier unit 34 itself may comprise folding, in a random manner, sheet material manufactured according to process described above, to form folds of said sheet material that are randomly oriented with respect to other folds. Alternatively, or additionally, a plurality of layers of said sheet may be layered (and optionally folded) to form the carrier unit 34.

The compression-resistant spacer 36 is located immediately downstream of the aerosol carrier unit 34 and abuts the aerosol carrier unit 34. In one of more embodiments of the present invention, the compression-resistant spacer 36 comprises a hollow tube. Optionally, the hollow tube may be formed from cellulose acetate. The compression-resistant spacer 36 is configured to locate the aerosol carrier unit 34 at the upstream end of the aerosol carrier cartridge 14 so that it can be penetrated by the heater element 24 of device 12. The compression-resistant spacer 36 may serve to inhibit downstream movement of the aerosol carrier unit 34 within the aerosol carrier cartridge 14 when the heater element 24 of device 12 is inserted into aerosol carrier unit 34. The compression-resistant spacer 36 also serves to space the cooling element 38 from the aerosol carrier unit 34.

The cooling element 38 is located immediately downstream of the compression-resistant spacer 36 and abuts the compression-resistant spacer 36. In use, the air stream entrained with an aerosol and/or vapour released from the aerosol carrier unit 34 pass through the cooling element 38 towards the second end 18 of the of the aerosol carrier cartridge 14. Hereinafter, compounds and/or flavours and/or any other substances released from the nicotine carrier unit 34, when heated by the heater element 24, shall be referred to as "substances". The air stream and aerosol substances entrained therein may cool within the cooling element 38 for inhalation by the user. In one or more embodiments of the present invention, cooling element 38 comprises a plurality of cooling formations 42 therein. Optionally, the formations 42 may comprise a plurality of longitudinal channels that extend along the length of the cooling element 38. Further optionally, these formations 42 may be formed by folding a sheet material to create a plurality of folded layers, optionally with the layers at random orientations to one another. Optionally, the cooling element 38 may comprise a polymer material.

The filter element 40 is located immediately downstream of the cooling element 38 and abuts the cooling element 38. In one or more embodiments of the present invention, the filter element 40 comprises a conventional filter.

The aerosol carrier cartridge 14 may be assembled by coaxially aligning the aerosol carrier unit 34, compression-resistant spacer 36, cooling element 38 and filter and inserting the components in this configuration into the housing 32.

The aerosol carrier cartridge 14 configured to engage with the device 12 comprising a heater element 24 in order to deliver aerosol to a user. In use, the heater element 24 of the device 12 heats the aerosol carrier unit 34 of the aerosol carrier cartridge 14 to a sufficient temperature to release (or liberate) captive substances held within the aerosol carrier unit 34 to form a vapour and/or aerosol, which is drawn downstream through the aerosol carrier cartridge 14 and inhaled by the user.

The compression-resistant spacer 36 of the aerosol carrier cartridge 14 is configured to resist the penetration force experienced by the aerosol carrier cartridge 14 during insertion of the heater element 24 of the device 12 into the aerosol carrier unit 34. The compression-resistant spacer 36 of the aerosol carrier cartridge 14 thereby may inhibit movement of the aerosol carrier unit 34 downstream within the aerosol carrier cartridge 14 during insertion of the heater element 24 of the device 12 into the aerosol carrier unit 34.

With the heater element 24 inserted into the aerosol carrier unit 34, operation of the device 12 will cause the heater element 24 to heat the aerosol carrier unit 34 of the aerosol carrier cartridge 14 to a temperature sufficient to release (or liberate) captive substances held within the aerosol carrier unit 34 to form a vapour and/or aerosol. At sufficiently high temperatures, substances are released from the aerosol carrier unit 34 of the aerosol carrier cartridge 14. As a user draws on second end 18 of the aerosol carrier cartridge 14, the released substances from the aerosol carrier unit 34 are drawn downstream through the aerosol carrier cartridge 14 (entrained in a stream of air) and condense to form an aerosol that is drawn through the filter element 40 of the aerosol carrier cartridge 14 into the user's mouth.

As the air with the entrained vapour and/or aerosol containing the released substance passes downstream thorough the cooling element 38 the temperature of the air stream and entrained vapour and/or aerosol substances may be reduced due to transfer of thermal energy from the air stream and entrained vapour and/or aerosol substances to the cooling element 38. This is to ensure that the temperature of the air stream and entrained vapour and/or aerosol substances is at a relatively low temperature when exiting the second end 18 of the aerosol carrier cartridge 14 so as to be comfortable for a user to inhale.

Figure 7:
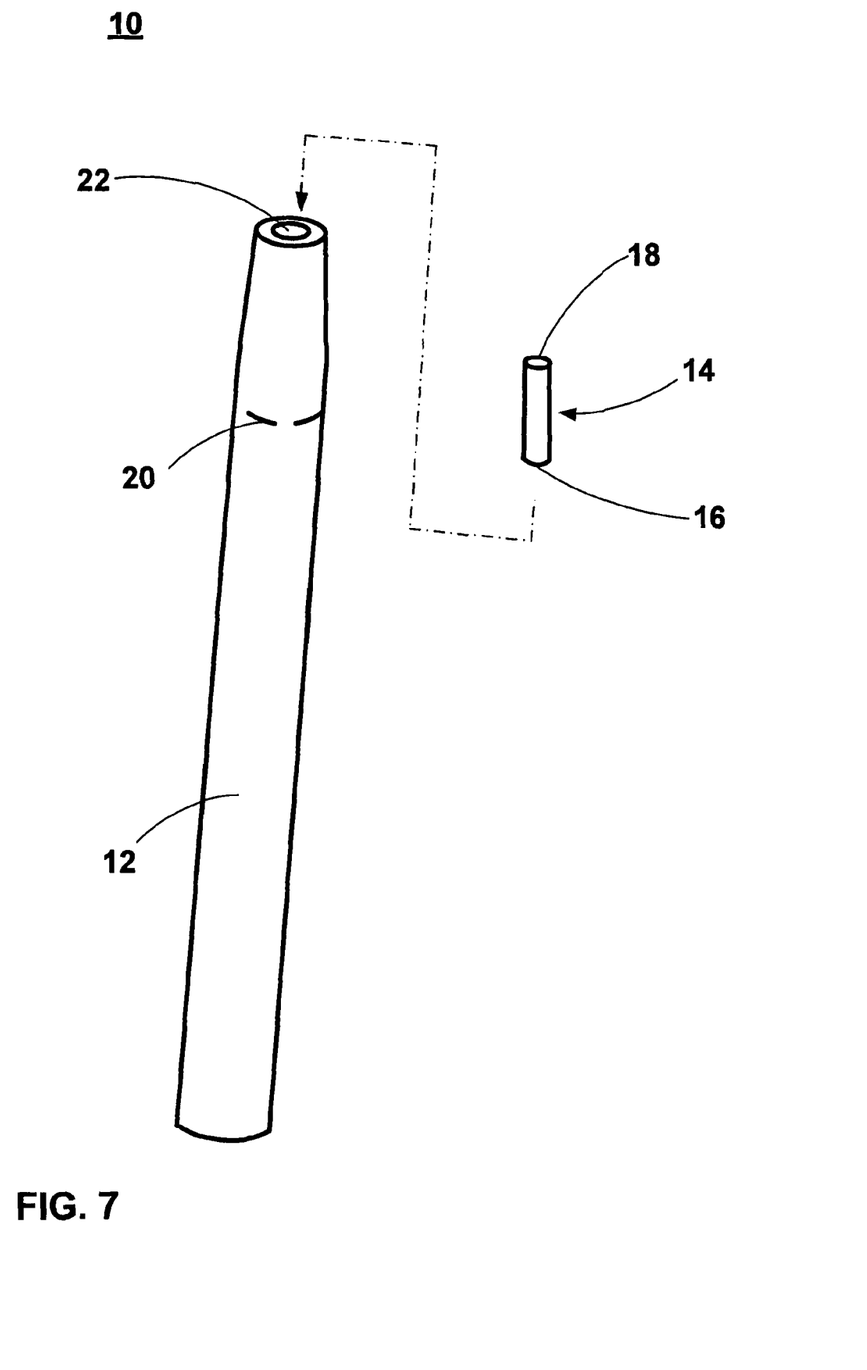
FIG. 7 is an exploded perspective view illustration of a kit-of-parts for assembling a system according to one or more embodiments of the present invention.

FIG. 7 is an exploded perspective view illustration of a kit-of-parts for assembling an aerosol delivery system 10 according to one or more embodiments of the present invention.

There has been described in the foregoing one or more embodiments of an aerosol delivery system that avoids or at least ameliorates the problems of the prior art.

In one or more optional arrangements, a carrier unit 34 containing nicotine and/or nicotine compounds may be substituted or supplemented with a carrier unit configured to provide a flavoured vapour and/or aerosol upon heating of the carrier unit by the heater element 24 of the device 12. A precursor material for forming the flavoured vapour and/or aerosol upon heating is held within pores, spaces, channels and/or conduits within the carrier unit. The precursor material may be extracted from a tobacco plant starting material using a supercritical fluid extraction process. Optionally, the precursor material is nicotine-free and comprises tobacco-flavours extracted from the tobacco plant starting material. Further optionally, the extracted nicotine-free precursor material (e.g. flavours only) could have nicotine added thereto prior to loading of the precursor material into the substrate of the carrier unit. Further optionally, flavours and physiologically active material may be extracted from plants other than tobacco plants.

In one or more optional arrangements, a carrier unit (containing nicotine, or nicotine-free) comprises two physically separate substrates. A first substrate is configured to hold a precursor material for forming a vapour and/or aerosol upon heating. A second substrate is configured to be penetrable by the heater element 24 of the device 12. In the one or more optional arrangements, the precursor material is not directly heated, which may be desirable in some instances (e.g. where direct heating may have a negative impact on flavours to be produced). Locating the precursor material in a different substrate to that which undergoes direct heating (i.e. the second substrate) means that the first substrate may experience lower temperatures than those experienced by the second substrate. In one or more embodiments the first substrate may be selected to have a thermal conductivity to provide a desired low-temperature at the second substrate or have a physical configuration which distributes the thermal energy from the heater element across the volume of the first substrate in order to dissipate the energy and produce a low heating effect at the second substrate. Therefore, different materials may be used for the first substrate than are used for the second substrate. Optionally, a thermally conductive barrier layer may be located between the first substrate and second substrate to separate the two substrates. Further optionally, the thermally conductive barrier layer may comprise a metal foil layer. However, heat transferred to the second substrate from the heater element 24 can still be transferred to the first substrate (to cause release of vapour and/or aerosol from the precursor material) via the thermally conductive barrier layer. The material of the first substrate comprises an absorbent material suitable for holding a quantity of precursor material. The material of the first substrate may comprise, for example, paper material, microporous foam material and/or microporous polymer material and/or ceramic material. The precursor material may optionally be impregnated into the material of the first substrate and/or may be coated onto surfaces of the first substrate. For example, the precursor material may comprise a liquid absorbed into the material of the first substrate and/or the precursor material may comprise a powder coated onto surfaces of the first substrate.

Figure 8:
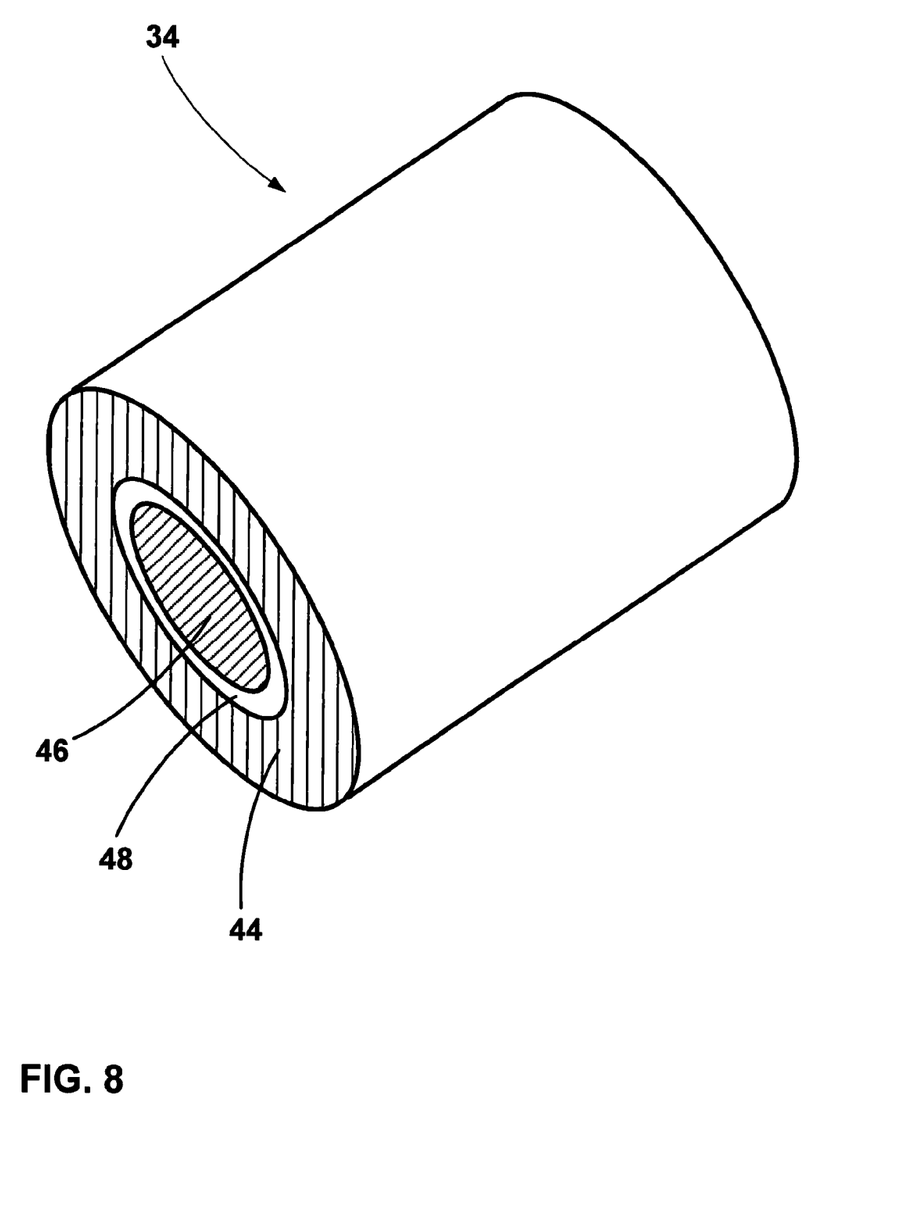
FIG. 8 is a perspective view illustration of an optional arrangement of a carrier unit of a carrier cartridge according to one or more embodiments of the present invention.

In one or more optional arrangements comprising a carrier unit having two separate substrates (see FIG. 8), the second substrate 46 may be formed into a cylinder and the first substrate 44 may be formed into an annular sleeve configured to fit around the second substrate 46. The optional thermally conductive barrier layer 48 may also be configured as an annular sleeve configured to fit around the second substrate 46 and around which the annular sleeve of the first substrate 44 can be fitted. In these arrangements precursor material containing flavours and/or nicotine may be held in the outer, first substrate 44. The inner, second substrate 46 is configured to be penetrable by the heater element 24 of device 12. Optionally, the material forming the second substrate 46 may comprise the types of material discussed above in relation to FIG. 5 and/or may comprise other types of materials suitable for penetration by the heater element 24 of device 12. In all optional arrangements, the material of the second substrate 46 comprises a heat-resistant material. This may avoid degradation (e.g. by pyrolysis) of the second substrate 46 when heat is applied to the second substrate 46 via the heater element 24. Optionally, the material forming the second substrate 46 may comprise a solid, relatively impenetrable material comprising a pre-formed bore, aperture or slot, for receiving the heater element 24 of device 12.

As used herein any reference to "one embodiment" or "an embodiment" means that a particular element, feature, structure, or characteristic described in connection with the embodiment is included in at least one embodiment. Any appearances of the phrase "in one embodiment" or the phrase "in an embodiment" in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A carrier unit for a nicotine carrier cartridge, the nicotine carrier unit comprising:
    a carrier substrate, the carrier substrate comprising an aerosol-forming precursor comprising a nicotine-containing and/or flavoured fluid, gel, wax, or powder; and
    a thermally conductive substrate, the thermally conductive substrate being formed into a cylinder that is configured to be pierced by a heater element of a device operative to initiate and maintain release of an aerosol from said carrier unit, such that penetration of the thermally conductive substrate by the heater element forms an aperture in the thermally conductive substrate;
    wherein the thermally conductive substrate is configured to conduct heat from the heater element to the carrier substrate to cause indirect heating of the carrier substrate to a lower temperature than that experienced by the thermally conductive substrate, and thereby cause release of said aerosol-forming precursor from the carrier substrate.

2. The carrier unit according to claim 1, wherein the carrier substrate comprises sheet material formed from heat-resistant material.

3. The carrier unit according to claim 2, wherein the sheet material is folded in a concertina arrangement.

4. The carrier unit according to claim 2, wherein said sheet material is folded in a random manner to form folds of said sheet material that are randomly oriented with respect to other folds of said sheet material.

5. The carrier unit according to claim 2, wherein said carrier substrate comprises a plurality of layers of sheet material, each layer oriented in a random manner with respect to other layers of said material.

6. The carrier unit according to claim 2, wherein the heat-resistant material comprises a paper or paper matrix composite.

7. The carrier unit according to claim 2, wherein the heat-resistant material comprises a plastic or plastic matrix composite.

8. The carrier unit according to claim 2, wherein the heat-resistant material comprises a ceramic or ceramic matrix composite.

9. The carrier unit according to claim 8, wherein the ceramic composite comprises alumina-silicate fibres.

10. The carrier unit according to claim 1, wherein the carrier substrate is impregnated with said aerosol-forming precursor.

11. The carrier unit according to claim 1, wherein the carrier substrate is coated with said aerosol-forming precursor.

12. The carrier unit according to claim 1, wherein the carrier substrate is configured to hold and release extracts from a tobacco plant.

13. The carrier unit according to claim 1, wherein an exterior surface of said carrier unit is formed from heat-resistant material configured to surround said carrier substrate.

14. The carrier unit according to claim 1, wherein the carrier substrate comprises an annular ring disposed around the thermally conductive substrate.

15. The carrier unit according to claim 1, wherein the carrier unit further comprises an isolation layer that separates the carrier substrate and the thermally conductive substrate to isolate the heater element from aerosol-generating precursor.

16. A kit-of-parts for assembling the aerosol delivery system of claim 1, comprising:
    the carrier cartridge; and
    the aerosol-generating device.

17. A carrier cartridge for a system for aerosol delivery, the carrier cartridge being the nicotine carrier cartridge of claim 1 and comprising the carrier unit of claim 1, the carrier cartridge at an end thereof configured for insertion into a heating chamber of a device operative to initiate and maintain release of an aerosol from the carrier unit in said carrier cartridge, and another end of said carrier cartridge configured for insertion into a mouth of a user.

18. The cartridge according to claim 17, wherein the carrier substrate comprises sheet material formed from heat-resistant material.

19. The cartridge according to claim 18, wherein the sheet material is folded in a concertina arrangement.

20. The cartridge according to claim 18, wherein said sheet material is folded in a random manner to form folds of said sheet material that are randomly oriented with respect to other folds of said sheet material.

21. The cartridge according to claim 18, wherein said substrate comprises a plurality of layers of sheet material, each layer oriented in a random manner with respect to other layers of said material.

22. The cartridge according to claim 18, wherein the carrier cartridge is tubular and comprises sheet material, and wherein a second end of the carrier cartridge is configured to form a mouthpiece for a user.

23. The cartridge according to claim 18, wherein the heat-resistant material comprises a paper or paper matrix composite.

24. The cartridge according to claim 18, wherein the heat-resistant material comprises a plastic or plastic matrix composite.

25. The cartridge according to claim 18, wherein the heat-resistant material comprises a ceramic or ceramic matrix composite.

26. The cartridge according to claim 25, wherein the ceramic composite comprises alumina-silicate fibres.

27. The cartridge according to claim 17, wherein the carrier substrate is impregnated with said aerosol-forming precursor.

28. The cartridge according to claim 17, wherein the carrier substrate is coated with said aerosol-forming precursor.

29. The cartridge according to claim 17, wherein the carrier substrate is configured to hold and release extracts from a tobacco plant.

30. The cartridge according to claim 17, wherein the carrier cartridge comprises a cooling element disposed adjacent to the carrier unit, the cooling element having a plurality of cooling formations which are a plurality of longitudinal channels that extend along the length of the cooling element for cooling fluid released from said aerosol-forming precursor during heating.

31. The cartridge according to claim 17, wherein said carrier cartridge further comprises a housing for said carrier unit.

32. The cartridge according to claim 17, wherein an exterior surface of said carrier unit is formed from heat-resistant material configured to surround said carrier substrate.

33. The cartridge according to claim 17, wherein the carrier substrate comprises an annular ring disposed around the thermally conductive substrate.

34. The cartridge according to claim 17, wherein the carrier unit further comprises an isolation layer that separates the carrier substrate and the thermally conductive substrate to isolate the heater element from aerosol-generating precursor.

35. An aerosol delivery system comprising:
the carrier cartridge of claim 17; and
an aerosol-generating device being the device operative to initiate and maintain release of the aerosol, the aerosol-generating device comprising:
  a device housing having the heating chamber of the device, the heating chamber being open-ended and configured to receive the carrier cartridge;
  a heater element disposed within the heating chamber and configured to receive at least a first end of the carrier cartridge, said heater element operable to heat the carrier substrate of the carrier unit of said carrier cartridge to cause release of the aerosol-forming precursor therefrom to generate the aerosol when gas is passed through the carrier cartridge.

36. The aerosol delivery system according to claim 35, wherein the carrier substrate comprises sheet material formed from heat-resistant material.

37. The aerosol delivery system according to claim 36, wherein the sheet material is folded in a concertina arrangement.

38. The aerosol delivery system according to claim 36, wherein said sheet material is folded in a random manner to form folds of said sheet material that are randomly oriented with respect to other folds of said sheet material.

39. The aerosol delivery system according to claim 36, wherein said carrier substrate comprises a plurality of layers of sheet material, each layer oriented in a random manner with respect to other layers of said material.

40. The aerosol delivery system according to claim 36, wherein the carrier cartridge is tubular and comprises sheet material, and wherein a second end of the carrier cartridge is configured to form a mouthpiece for a user.

41. The aerosol delivery system according to claim 36, wherein the heat-resistant material comprises a paper or paper matrix composite.

42. The aerosol delivery system according to claim 36, wherein the heat-resistant material comprises a plastic or plastic matrix composite.

43. The aerosol delivery system according to claim 36, wherein the heat-resistant material comprises a ceramic or ceramic matrix composite.

44. The aerosol delivery system according to claim 43, wherein the ceramic composite comprises alumina-silicate fibres.

45. The aerosol delivery system according to claim 35, wherein the carrier substrate is impregnated with said aerosol-forming precursor.

46. The aerosol delivery system according to claim 35, wherein the carrier substrate is coated with said aerosol-forming precursor.

47. The aerosol delivery system according to claim 35, wherein the carrier substrate is configured to hold and release extracts from a tobacco plant.

48. The aerosol delivery system according to claim 35, wherein the carrier cartridge comprises a cooling element disposed adjacent to the carrier unit, the cooling element having a plurality of cooling formations which are a plurality of longitudinal channels that extend along the length of the cooling element for cooling fluid released from said aerosol-forming precursor during heating.

49. The aerosol delivery system according to claim 35, wherein said carrier cartridge further comprises a housing for said carrier unit or for said carrier unit and said cooling element.

50. The aerosol delivery system according to claim 35, wherein an exterior surface of said carrier unit is formed from heat-resistant material configured to surround said carrier substrate.

51. The aerosol delivery system according to claim 35, wherein the carrier substrate comprises an annular ring disposed around the thermally conductive substrate.

52. The aerosol delivery system according to claim 35, wherein the carrier unit further comprises an isolation layer that separates the carrier substrate and the thermally conductive substrate to isolate the heater element from aerosol-generating precursor.

* * * * *